US008193172B2

(12) United States Patent
Sennef et al.

(10) Patent No.: US 8,193,172 B2
(45) Date of Patent: Jun. 5, 2012

(54) METHODS FOR THE TREATMENT OF MAJOR DEPRESSIVE DISORDER USING GLUCOCORTICOID RECEPTOR ANTAGONISTS

(75) Inventors: Cornelis C. Sennef, BH Oss (NL); Bernardus Wijnand Mathys Marie Peeters, BH Oss (NL)

(73) Assignee: Pop Test Cortisol LLC, Cliffside Park, NJ (US)

( * ) Notice: Subject to any disclaimer, the term of this patent is extended or adjusted under 35 U.S.C. 154(b) by 1356 days.

(21) Appl. No.: 10/496,222

(22) PCT Filed: Nov. 18, 2002

(86) PCT No.: PCT/EP02/12854
§ 371 (c)(1),
(2), (4) Date: Sep. 10, 2004

(87) PCT Pub. No.: WO03/043640
PCT Pub. Date: May 30, 2003

(65) Prior Publication Data
US 2005/0020480 A1 Jan. 27, 2005

(30) Foreign Application Priority Data

Nov. 23, 2001 (EP) .................................. 01204518

(51) Int. Cl.
*A61K 31/58* (2006.01)
(52) U.S. Cl. ....................................................... 514/174
(58) Field of Classification Search .................... 514/174
See application file for complete search history.

(56) References Cited

U.S. PATENT DOCUMENTS 4,814,333 A 3/1989 Ravaris

FOREIGN PATENT DOCUMENTS

| EP | 0763541 A1 * | 8/1996 |
| EP | 0 763541 A1 | 3/1997 |
| EP | 0 683 172 B1 | 8/1997 |
| WO | WO 99/17779 * | 4/1999 |
| WO | WO 00/66522 | 11/2000 |
| WO | WO 02/17895 A2 | 3/2002 |
| WO | WO 02/17895 A3 | 3/2002 |
| WO | WO 02/076390 A2 | 10/2002 |

OTHER PUBLICATIONS

Carroll et al., "Urinary free cortisol excretion in depression," *J. Psychol. Med.* 6(1976) 43-47.
Gibbons et al., "Plasma cortisol in depressive illness," *Psychiatr. Res.* 1, (1963) 162-171.
Gold et.al., "Clinical and biochemical manifestations of depression: relation to the neurobiology of stress," *New England J. Med.* 319(1988) 413-420.
Halbreich et.al., "Cortisol secretion in endogenous depression, II, time related functions," *Archs. Gen. Psychiat.* 42(1985) 909-914.
Halbreich, et.al., "The Mean 1300-1600 h Plasma Cortisol Concentration as a Diagnostic Test for Hypercortisolism," *J. Clin. Endocrinol. Metab* 54(1982) 1262-1264.
Hamilton, M., "A rating scale for depression," *J. Neurol. Neurosurg. Psychiat.* 23(1960) 56-62.
Hanada et.al., "Direct radioimmunoassay of cortisol in saliva and its application to the dexamethasone suppression test in affective disorders," *Psychoneuroendocrinology* 10(1985) 193-201.
Holsboer et al., "Antidepressants and Hypothalamic-Pituitary-Adrenocortical regulation," *Endocrine Reviews* 17(1996) 187-205.
Linkowski et.al., "The 24-hour profile of adrenocorticotropin and cortisol in major depressive illness," *J. Clin. Endocrinol. Metab.* 61(1985) 429-438.
McClure, DJ, "The effects of antidepressant medication on the diurnal plasma cortisol levels in depressed patients," *J. Psychosom. Res.* 10(1966) 197-202.
Murphy et.al., "Possible Use of Glucocorticoid Receptor Antagonists in the Treatment of Major Depression: Preliminary Results Using RU 486," *J. Psychiat. Neurosc.* 18(1993) 209-213.
Murphy, B.E.P., "Steroids and Depression," *J. Steroid Biochem. Mol. Biol.* 38(1991) 537-558.
Penta et.al., "Mouse and Large-Animal Toxicology Studies of Twelve Antitumor Agents: Relevance to Starting Dose for Phase I Clinical Trials," *Cancer Chemother. Pharmacol.* 3(1979) 97-101.
Poland et al., "Saliva cortisol levels following dexamethasone administration," *Life Sci.* 30(1982) 177-181.
Rosenbaum et al., "Towards a biochemical classification of depressive disorders, VII: urinary free cortisol and urinary MHPG in depression," *Am. J. Psychiat.* 140(1983) 314-318.
Schöbitz et.al., "The Role of the Hypothalamic-Pituitary-Adrenocortical System during Inflammatory Conditions," *Critical Reviews in Neurobiology* 8(1994 ) 263-291.
Sherman et.al., "Circadian analysis of plasma cortisol before and after dexamethasone administration in depressed patients," *Archs. Gen. Psychiat.* 41(1984) 271-275.
Murphy, Beverly, et al, Neuroendocrine Responses to Inhibitors of Steroid Biosynthesis in Patients with Major Depression Resistant to Antidepressant Therapy.
Bertagna, Xavier et al, The New Steroid Analog RU 486 Inhibits Glucocorticoid Action in Man, Journal of Clinical Endocrinology and Metabolism, 1984, 25-28, vol. 59, No. 1.
Bertagna, X. et al, Administration of RU 486 for 8 Days in Normal Volunteers: Antiglucocorticoid Effect with No Evidence of Peripheral Cortisol Deprivation, Journal of Clinical Endocrinology and Metabolism, 1994, 375-380, vol. 78, No. 2.

(Continued)

*Primary Examiner* — Barbara P Badio
(74) *Attorney, Agent, or Firm* — Arthur Jacob

(57) ABSTRACT

The present invention relates to a method for the treatment of a patient suffering from major depressive disorder by administering to the patient an effective amount of a glucocorticoid receptor antagonist and to methods for establishing the optimal treatment regimen.

4 Claims, 1 Drawing Sheet

OTHER PUBLICATIONS

Gaillard et al, RU 486: A steroid with antiglucocorticosteroid activity that only disinhibits the human pituitary-adrenal system at a specific time of day, Proc. Natl. Acad. Sci. USA, Jun. 1984, 3879-3382, vol. 81.

Heikinheimo, Oskari et al, Termination of Pregnancy with Mifepristone and Prostaglandin Suppresses Transiently Circulating Glucocorticoid Bioactivity, The Journal of Clinical Endocrinology & Metabolism, 2003, 323-326, vol. 88.

Laue, Louisa et al, Effect of Chronic Treatment with the Glucocorticoid Antagonist RU 486 in Man: Toxicity, Immunological, and Hormonal Aspects, Journal of Clinical Endocrinology and Metabolism, 1990, 1474-1480, vol. 71, No. 6.

\* cited by examiner

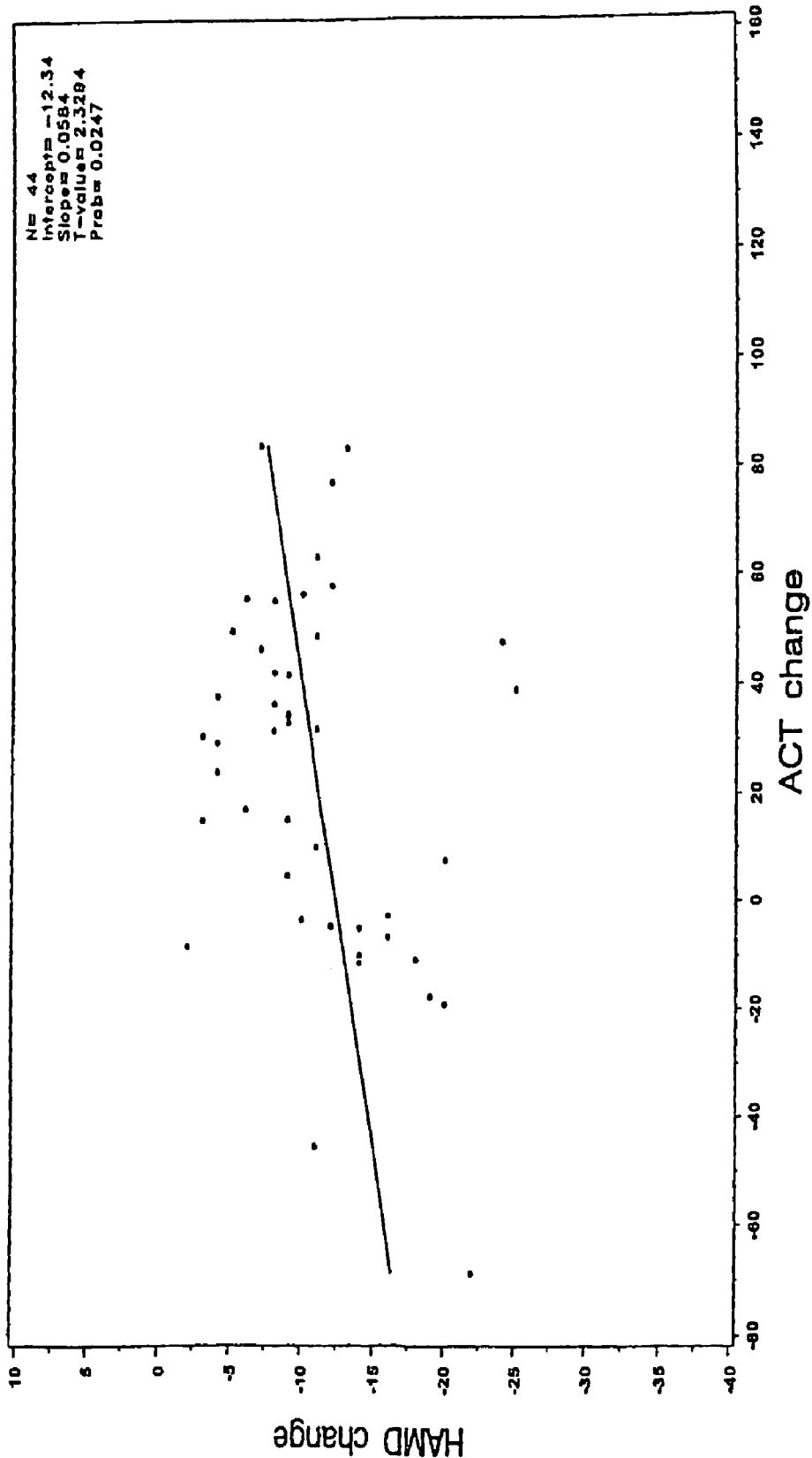
Correlation between HAMD-21 change, scored at day 14 of treatment, and cortisol (ACT) change at the end (28 days) of treatment for patients which received a daily dose of 150-300 mg of Org 34517.

METHODS FOR THE TREATMENT OF MAJOR DEPRESSIVE DISORDER USING GLUCOCORTICOID RECEPTOR ANTAGONISTS

RELATED APPLICATIONS

This application is a US national stage filing of PCT/EP02/12854, filed on Nov. 18, 2002, claiming priority to EP 01204518.3, filed on Nov. 23, 2001.

FIELD OF THE INVENTION

The present invention relates to a method for the treatment of a patient suffering from major depressive disorder by administering to the patient an effective amount of a glucocorticoid receptor antagonist and to methods for establishing the optimal treatment regimen.

BACKGROUND OF THE INVENTION

Major depressive disorder is a psychiatric disorder which has a lifetime prevalence of around 8%. One of the most consistent findings in psychiatry is that patients with major depression present with alterations in the hypothalamic-pituitary-adrenal (HPA) axis. A significant percentage of depressed patients exhibit hypersecretion of the adrenal glucocorticosteroid cortisol, as manifested by elevated plasma and cerebrospinal fluid concentrations of cortisol and increased urinary free cortisol. In addition many depressed patients exhibit a clear inability to switch off endogenous cortisol release following exogenous challenge with the potent synthetic glucocorticoid dexamethasone (the so-called dexamethasone non-suppressors) (Gold P. W., et al., *Clinical and biochemical manifestations of depression: relation to neurobiology of stress*. New England J. Med. 319, 413-420, 1988). This 'sub-group' of severely compromised patients are most often the ones in whom depression becomes a life-threatening illness that warrants hospitalisation. Other abnormalities of the HPA axis found in depressed patients are increased cortisol response to corticotrophin, a blunted corticotrophin response to CRH (corticotrophin releasing hormone), and adrenal and pituitary enlargement (for a review see Holsboer, F. and Barden, N.: *Antidepressants and Hypothalamic-Pituitary-Adrenocortical regulation*. Endocrine Reviews 1996, 17, 187-205). These observations have been interpreted to suggest a causal relationship between disturbed functioning of the HPA axis and the pathology of depression (Murphy, B. E. P.: Steroids and Depression. J. of Steroid Biochem. and Mol. Biol. 1991, 38, 537-559). Therapeutic efficacy of classical antidepressants has been shown to be preceded by or to coincide with restoration of the disturbed HPA axis in depression (Holsboer and Barden, 1996, supra). It has been postulated that any intervention which can restore this HPA dysfunction may have antidepressant potential. One type of such intervention is the administration of glucocorticoid synthesis inhibitors, as has been shown in patient suffering from Cushing's syndrome, which is a conditions in which high cortisol levels are reported as a result of adrenal gland malfunction (due to a pituitary tumour or a secondary tumour, both producing the cortisol secretagogue ACTH). The depressive symptoms associated with Cushing's disappear relatively quickly with the return of cortisol levels to normal. Such treatment may involve removal of the offending tumour or treatment with cortisol synthesis inhibitors such as metyrapone, ketoconozole, or aminoglutethimide (Murphy, B. E. P., *Steroids and Depression*. J. Steroid Biochem & Mol. Biol. 38, 537-558, 1991). Similarly, relatively recent clinical trials have demonstrated that cortisol synthesis inhibitors can be used to ameliorate depressive symptoms in severe, treatment-resistant non-Cushing depressives (Murphy, B. E. P., *Neuroendocrine responses to inhibitors of steroid synthesis in patients with major depression resistent to antidepressant therapy*. Can. J. Psych. 43, 279-286, 1998; see also U.S. Pat. No. 4,814,333 (Ravaris, C. L.): *Method for treatment of hypercortisolemic, depressed patients*.). Drawbacks of the use of cortisol synthesis inhibitors to lower plasma cortisol levels are their high toxicity and their relatively low degree of selectivity for inhibition of cortisol synthesis versus synthesis of other endogenously manufactured steroids (such as mineralocorticoids and sex steroids) which can result in adrenal insufficiencies. A further serious disadvantage is that the onset of therapeutic effect of these cortisol synthesis inhibitors is as long as that observed with classical antidepressants (e.g., several weeks).

Another type of intervention is the use of direct glucocorticoid receptor (GR) antagonists, which have much more specific pharmacological effects as compared to synthesis inhibitors and which may help restore HPA activity. Small scale pilot clinical studies have been conducted in order to study the antidepressant activity of the non-selective glucocorticoid receptor antagonist RU 486 (mifepristone; 17β-hydroxy-11β-(4-dimethylaminophenyl)-17α-(1-propynyl) estra-4,9-dien-3-one; Murphy, B. E. P. et al. J. Psychiat. Neurosc. 18, 209-213, 1993). Relatively high dose mifepristone, in the range of 8-12 mg/kg/day, over a relatively short period of time (4 days), was also shown to be effective in the treatment of psychosis associated with psychotic major depression (International Patent Application WO 99/17779; Schatzberg and Belanoff). More recently (Nemeroff, C., Remeron Scientific Expert Meeting, Budapest, Mar. 29-Apr. 1, 2001) it was demonstrated in a Phase IIB continuation of this study, that both the number of responders as well as the efficacy of the psychosis treatment increased with increasing daily dose of mifepristone as measured by the change in Brief Psychiatric Rating Scale (50 mg—33% change; 600 mg—40% change and 1200 mg—52% change). These data indicate that a higher dose of glucocorticoid receptor antagonist is correlated with a higher clinical efficacy.

Glucocorticoids are extremely important hormones, which play key roles in the coping mechanisms that animals (including man) have at their disposal against internal and external stressors. Pharmacologically effective dosages of glucocorticoid receptor antagonists will block physiological action of endogenous glucocorticoids and may thereby induce risks when stressors affect the organism. It has for instance been explained [Schöbitz et al. Critical Reviews in Neurobiology (1994) 8 (4), 263-291] that corticosteroids are crucial for the control of inflammatory processes since they inhibit the production of cytokines. Glucocorticoid antagonism may lead to increased levels of pro-inflammatory cytokines. In general it can be stated that the higher the daily doses of a glucocorticoid receptor antagonist applied the higher the risk of unwanted side effects caused by non-selective actions. Thus there remains a great need for treatment regimens for patients suffering from major depressive disorder (MDD) which is both effective and safe.

SUMMARY OF THE INVENTION

The present invention fulfills this need by providing a method for the treatment of a patient suffering from major depressive disorder by administering to the patient an effective amount of a glucocorticoid receptor antagonist characterized in that the highest daily dose is selected which does not increase the peripheral cortisol level.

BRIEF DESCRIPTION OF THE FIGURES

FIG. 1 is an illustration of the correlation between MAMD-21, scored at day 14 and cortisol change determined at 28 days of treatment for patients receiving a daily dose of 150-300 mg Org 34517.

DETAILED DESCRIPTION OF THE INVENTION

The glucocorticoid receptor antagonist used in the method of the invention can be either a steroidal or a non-steroidal antagonist. Steroidal glucocorticoid receptor antagonists, such as RU 486 (supra) and especially the strong antiglucocorticoids with low anti-progestational activity such as (11β,17α)-11-[4-(dimethylaminlo)phenyl]-17-hydroxy-21-[4-(methylsulfonyl)phenyl]-19-norpregna-4,9-dien-20-yn-3-one and derivatives as disclosed in European Patent 0683 172 B1 (Akzo Nobel N.V.), are preferred. In a further preferred embodiment of the invention, the steroidal glucocorticoid receptor antagonists to be used in the method of the invention is selected from compounds which are highly active in vivo showing predominant anti-glucocorticoid activity, while lacking appreciable affinity for mineralocorticoid, progesterone, oestrogen and androgen receptors. More specifically, these preferred steroidal glucocorticoid receptor antagonists for use in the method of the invention are the 11-(substituted phenyl)-estra-4,9-diene derivatives of formula I, described in European Patent EP 0763 541 B1 (Akzo Nobel N.V.),

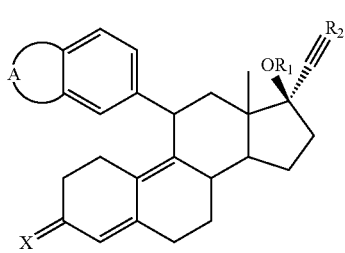
(I)

wherein A is a residue of a 5- or 6-membered ring containing 2 heteroatoms which are not connected to each other and are independently selected from O and S, the ring being optionally substituted with one or more halogen atoms; or A is a residue of a 5-6-membered ring wherein no double C—C bonds are present, containing 1 heteroatom selected from O and S, which heteroatom is connected to the phenyl group at the position indicated with an asterix, the ring being optionally substituted with one or more halogen atoms; $R_1$ is H or 1-oxo(1-4C)alkyl; $R_2$ is H or (1-8C)alkyl, halogen or $CF_3$; and X is selected from (H,OH), O, and NOH.

Compounds of formula I wherein the heteroatom(s) are (is) O, the 5- or 6-membered ring being optionally substituted with one or more fluorine atoms; $R_1$ is H; $R_2$ is methyl; and X is O or NOH are especially preferred.

A preferred compound according to the above formula I is (11β,17β)-11-(2,3-dihydro-1,4-benzodioxin-6-yl)-17-hydroxy-17-(1-propynyl)estra-4,9-dien-3-one. The most preferred compound for use in the methods of the present invention is the glucocorticoid receptor antagonist (11β,17β)-11-(1,3-benzodioxol-5-yl)-17-hydroxy-17-(1-propynyl)estra-4,9-dien-3-one, hereafter referred to as Org 34517, which can be prepared as described in EP 0763 541 B1 (supra), the contents of which are herein incorporated by reference.

In the method of the invention the highest daily dose is selected which does not increase the peripheral cortisol level. Peripheral cortisol level, as opposed to the cortisol level in the central nervous system, means the cortisol concentration in body fluids such as urine, saliva, blood and plasma. These cortisol concentration can be determined by methods of analysis known in the art. For instance cortisol concentrations in plasma can be determined as described by Gibbons and McHugh [*Plasma cortisol in depressive illness*. Psychiatr. Res. 1 (1963), 162-171] or by McCure [*The effects of antidepressant medication on the diurnal plasma cortisol levels in depressed patients*. J. Psychosom. Res. 10 (1966), 197-202] and Sherman et al. [*Circadian analysis of plasma cortisol before and after dexamethasone administration in depressed patients*. Archs. Gen. Psychiat. 41 (1984), 271-275]. Urine cortisol concentration can be determined as described by Caroll et al. [*Urinary-free cortisol excretion in depression*. J. Psychol. Med. 6 (1976) 43-47] or by Rosenbaum et al. [*Towards a biochemical classification of depressive disorders, VII: urinary free cortisol and urinary MHPG in depression* Am. J. Psychiat. 140 (1983), 314-317], while concentrations in saliva can be determined as described by Poland and Rubin [*Saliva cortisol levels following dexamethasone administration*. Life Sci. 30 (1982), 177-181] or by Hanada et al. [*Direct radioimmunoassay of cortisol in saliva and its application to the dexamethasone suppression test in affective disorders*. Psychoneuroendocrinology 10 (1985), 193-201]. Saliva is the body fluid most preferred because it is the most convenient to obtain.

Because the peripheral cortisol concentration in a patient changes with a 24 hours cycle, as for instance described by Halbreich et al [*Cortisol secretion in endogenous depression, II, time related functions*. Archs. Gen. Psychiat. 42 (1985), 909-914] or by Linkowski et al. [*The 24-hour profile of adrenocorticotropin and cortisol in major depressive illness*. J. Clin. Endocrinol. Metab. 61 (1985) 429], it will be understood that changes in peripheral cortisol level in a patient relate to changes in concentrations of cortisol in a particular body fluid as measured on differing days but in samples taken at the same time on each day.

There is no increase in the peripheral cortisol level in a particular body fluid, be it either urine, plasma, blood or saliva, when the successive day to day measurements of the cortisol concentration yield values which stay within the standard deviation characteristic for the specific method of analysis used.

The selection of the highest daily dose of glucocorticoid receptor antagonist which does not increase the peripheral cortisol concentration can be carried out using either an up-titration regimen or a down-titration.

In a preferred method according to the invention the daily dose is selected using an up-titration regimen characterized by the following steps:
(a) measuring the peripheral cortisol level at day 0;
(b) administration of the minimal effective dose of the antagonist for 3 days;
(c) measuring the peripheral cortisol level on day 3;
(d) administration of an increased dose of antagonist in case the cortisol level on day 3 is not increased as compared with the level on day 0;
(e) repeating steps (c) and (d) until the dose Z is determined which results in an increased periphiral cortisol level as compared with day 0;
(f) administration during four weeks of the highest dose (Z-1) which did not lead to an increased cortisol level; or (g) in patients wherein the dose Z cannot be determined, administration during four weeks of the maximum tolerated dose.

In this regimen the starting dose of glucocorticoid receptor antagonist of step (b) of the regimen is the minimal effective dose, which is the first dose in a dose finding study with the particular glucocorticoid receptor antagonist which results in a statistically significant effect with respect to a relevant parameter for major depressive disorder. A suitable parameter is the HAMD score (Hamilton Rating Scale for Depression) score, a widely used test to evaluate the severity of depressive illness quantitatively. Another example of a suitable effectivity parameter is the Clinical Global Impression (CGI) Scale [Guy, W. (1976): ECDEU. Assessment Manual for Psychopharmacology (revised) US DHEW Pub. No. (ADM) 76-338. US Government Printing Office, Wash. D.C.].

The increase of the dose applied in step (d) of the up-titration regimen increases either arithmatically by equal amounts (e.g. x, 2x, 3x, 4x, etc), or by approximately equal percentages (e.g. x, 2x, 4x, 8x,) or according to a specific formula (e.g. the modified Fibonacci dose escalation scheme of x, 2x, 3.3x, 5x, 7x, 9x, 12x and 16x: Penta et al. Cancer Chemother. Pharmacol. (1979), 3, 97-101). In practice the dose increments will usually correspond to one or multiple dosage units, each dosage unit containing a discrete amount of the particular glucocorticoid antagonist.

Step (g) in the up-titration regimen refers to those patients in which no increased cortisol level can be measured even when the daily dose has been increased up to the maximum tolerated dose (MTD). Such patients will than be treated for 4 weeks with the MTD. The maximum tolerated dose is known to the skilled person as the top or plateau of the dose-response relationship in terms of safety [details on dosing schedules are described in Chapter 14 of the standard reference *Guide to Clinical Trials*, by B. Spilker, Raven Press New York, 1991].

In another method according to the invention the daily dose is selected using an down-titration regimen characterized by the following steps:
(a) measuring the peripheral cortisol level at day 0;
(b) administration of the maximum tolerated dose of the antagonist for 3 days;
(c) measuring the peripheral cortisol level on day 3;
(d) administration of a decreased dose of antagonist in case the cortisol level on day 3 is increased as compared with the level on day 0;
(e) repeating steps (c) and (d) until the dose Y is determined which does not result in an increased peripheral cortisol level;
(f) administration during four weeks of the dose Y.

In the most preferred embodiment of the method of the invention the selective glucocorticoid antagonist (11β,17β)-11-(1,3-benzodioxol-5-yl)-17-hydroxy-17-(1-propynyl)estra-4,9-dien-3one (Org 34517) is used. In an up-titration regimen using Org 34517 a starting dose (step b) of 25 mg may be used, while the increased doses are determined using a dose increment corresponding to multiples of a dosage unit of 75 mg. The following schedule of increasing doses of Org 34517 can be applied: 25 mg, 75 mg, 150 mg, 300 mg, 450 mg, 600 mg, 750 mg and 900 mg (MTD).

A down-titration regimen using Org 34517 in the method of the invention can start with the maximum tolerated daily dose of 900 mg, followed by a schedule of decreasing doses 750 mg, 600 mg, 450, mg, 300 mg, 150 mg and 25 mg.

Pharmaceutical preparations, or compositions, for use in the method of the invention comprise a glucocorticoid receptor antagonist in admixture with pharmaceutically acceptable auxiliaries. The term "acceptable" means being compatible with the other ingredients of the composition and not deleterious to the recipients thereof. The compositions can be prepared in accordance with standard techniques such as those described in the standard reference Gennaro A. R. et al., Remington: *The Science and Practice of Pharmacy*, (20th ed., Lippincott Williams & Wilkins, 2000, Part 5: Pharmaceutical Manufacturing).

Compositions include e.g. those suitable for oral, buccal, sublingual, nasal or rectal administration, and the like, all in unit dosage forms for administration.

For oral administration, the active ingredient may be presented as discrete dosage units, such as tablets, capsules, powders, granulates, solutions, and suspensions.

The invention is illustrated in the following examples:

EXAMPLE 1

Treatment of Major Depressive Disorder Patients with Org 34517.

A double blind, 4 week, paroxetine controlled study of Org 34517 in depressed patients was carried out. Paroxetine is a selective serotonin re-uptake inhibitor which is recognized as an effective antidepressant for major depression. Patients were selected which had a primary depressive disorder fulfilling the diagnostic criteria of a Major Depressive Disorder (MDD) as defined by the DSM-IV for recurrent (296.3) episodes, and who had a severity of depression which resulted in a total score of at least 22 on the HAMD-21 (Hamilton Rating Scale for Depression; see Hamilton, M. "*A rating scale for depression.*" J. Neurol. Neurosurg. Psychiat. 1960, 23, 56-62) scale at baseline. Patient had an episode of depression which had lasted at least 2 weeks before baseline.

Patients were randomly allocated to one of three treatment groups. Group I patients (50 patients) received 2 capsules with 75 mg of Org 34517 and one placebo (total daily dose 150 mg) for the first 2 weeks and 2 capsules with 75 mg Org 34517 and 1 capsule with 150 mg (total daily dose 300 mg) the next 2 weeks; Group II patients (46 patients) received 3 capsules with 150 mg Org 34517 (total daily dose 450 mg) in the first 2 weeks and 4 capsules of Org 34517 (total daily dose 600 mg) in the next 2 weeks; Group III patients (44 patients) received 2 capsules with 10 mg paroxetine and one placebo capsule (total daily dose 20 mg) for the first 2 weeks, followed by 2 capsules of 10 mg and one capsule of 20 mg paroxetine (total daily dose 40 mg) in the next 2 weeks. Medication was administered orally in the morning. Efficacy assessment was done on days 4, 7, 10, 14, 21, 28 and 35 by using the 21-item HAMD scale.

FIG. 1 shows the significant (p=0.02) correlation between HAMD-21 change, scored at day 14 of treatment, and cortisol (ACT) change, determined at the end (28 days) of treatment for patients which received a daily dose of 150-300 mg of Org 34517. The most prominent clinical improvement (HAMD decrease) is seen in patients were cortisol is not increased. The cortisol levels were determined using the afternoon cortisol test (ACT) as described by Halbreich et al. [J. Clin. Endocrinol. Metab. (1982) 54 (6), 1262].

We claim:

1. A method for treatment with the compound (11β, 17β)-11-(1,3-benzodioxol-5-yl)-17-hydroxy-17-(1-propynyl)estra-4,9-dien-3-one of a patient suffering from major depressive disorder by determining, prior to treatment, a peripheral cortisol level at a selected time of day, then measuring peripheral cortisol level, at the selected time of day, after administering at least one daily dose of the compound to the patient, and continuing administration of the compound with a daily dose which, on the basis of corresponding daily measurements of peripheral cortisol level, is determined to be the highest daily dose that does not increase the peripheral cortisol level beyond the peripheral cortisol level measured prior to treatment.

2. The method of claim 1 wherein the selected time of day is in the afternoon.

3. A method for treatment with the compound (11β,17β)-11-(1,3-benzodioxol-5-yl)-17-hydroxy-17-(1-propynyl)estra-4,9-dien-3-one of a patient suffering from major depressive disorder by determining, prior to treatment, a peripheral cortisol level at a selected time of day, then measuring peripheral cortisol level, at the selected time of day, after administering at least one daily dose of the compound to the patient, and continuing administration of the compound with a daily dose selected from the list consisting of 25 mg, 150 mg, 300 mg, 450 mg, 600 mg, 750 mg and 900 mg by selecting the amount in the list immediately below that which, on the basis of corresponding daily measurements of peripheral cortisol level, is determined to be the highest daily dose that does not increase the peripheral cortisol level beyond the peripheral cortisol level measured prior to treatment.

4. The method of claim 3 wherein the selected time of day is in the afternoon.

* * * * *